United States Patent
Hawthorne et al.

(10) Patent No.: US 10,841,312 B2
(45) Date of Patent: *Nov. 17, 2020

(54) GENOME SHARING

(71) Applicant: 23andMe, Inc., Sunnyvale, CA (US)

(72) Inventors: Brian Lee Hawthorne, San Francisco, CA (US); Oleksiy Khomenko, Stanford, CA (US); Jeffrey Mellen, San Francisco, CA (US); Marcela Miyazawa, Mountain View, CA (US); Michael Polcari, San Francisco, CA (US); Jack Tihon, San Francisco, CA (US); Alexander Wong, Palo Alto, CA (US); Anne Wojcicki, Palo Alto, CA (US); Linda Avey, Lafayette, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,254

(22) Filed: Dec. 20, 2019

(65) Prior Publication Data
US 2020/0137063 A1 Apr. 30, 2020

Related U.S. Application Data

(63) Continuation of application No. 15/046,257, filed on Feb. 17, 2016, now Pat. No. 10,516,670, which is a (Continued)

(51) Int. Cl.
*G06F 7/00* (2006.01)
*H04L 29/06* (2006.01)
(Continued)

(52) U.S. Cl.
CPC .......... *H04L 63/101* (2013.01); *G06F 15/16* (2013.01); *G06F 16/9535* (2019.01);
(Continued)

(58) Field of Classification Search
None
See application file for complete search history.

(56) References Cited

U.S. PATENT DOCUMENTS 6,703,228 B1 * 3/2004 Landers .............. C12Q 1/6827
435/91.2
7,062,752 B2 6/2006 Simpson et al.
(Continued)

FOREIGN PATENT DOCUMENTS

WO WO 2009/051768 4/2009
WO WO 2016/073953 5/2016

OTHER PUBLICATIONS

U.S. Office Action dated Aug. 9, 2017 in U.S. Appl. No. 15/046,257.
(Continued)

*Primary Examiner* — Eliyah S. Harper
(74) *Attorney, Agent, or Firm* — Weaver Austin Villeneuve & Sampson LLP; David K. Buckingham

(57) ABSTRACT

Sharing data is disclosed. In some cases, sharing data includes receiving a request to share data from a first account to a second account, receiving an indication of a plurality of first account profiles associated with the first account to share with the second account, and establishing sharing from the plurality of first account profiles to the second account, wherein sharing comprises the second account having read access to a subset of nonpublic data associated with the plurality of first account profiles.

30 Claims, 16 Drawing Sheets

Related U.S. Application Data continuation of application No. 12/288,014, filed on Oct. 14, 2008, now Pat. No. 9,336,177.

(60) Provisional application No. 61/070,321, filed on Mar. 19, 2008, provisional application No. 60/999,148, filed on Oct. 15, 2007, provisional application No. 60/999,064, filed on Oct. 15, 2007.

(51) Int. Cl.
| | | |
|---|---|---|
| *G06F 16/9535* | (2019.01) | |
| *G06F 15/16* | (2006.01) | |
| *H04L 29/08* | (2006.01) | |
| *G06F 16/958* | (2019.01) | |
| *G16B 20/00* | (2019.01) | |
| *G06F 21/62* | (2013.01) | |

(52) U.S. Cl.
CPC .......... *H04L 67/306* (2013.01); *G06F 16/958* (2019.01); *G06F 21/6254* (2013.01); *G16B 20/00* (2019.02)

(56) References Cited

U.S. PATENT DOCUMENTS

| | | | | |
|---|---|---|---|---|
| 7,076,504 | B1* | 7/2006 | Handel | G06Q 30/02 705/14.39 |
| 7,292,944 | B2* | 11/2007 | Larder | G01N 33/5091 702/19 |
| 7,630,986 | B1* | 12/2009 | Herz | G06Q 10/10 |
| 7,783,665 | B1* | 8/2010 | Tormasov | G06F 16/176 707/783 |
| 7,818,396 | B2* | 10/2010 | Dolin | G06Q 30/02 709/217 |
| 7,957,907 | B2 | 6/2011 | Sorenson et al. | |
| 8,187,811 | B2 | 5/2012 | Eriksson et al. | |
| 8,428,886 | B2 | 4/2013 | Wong et al. | |
| 8,463,554 | B2* | 6/2013 | Hon | G06N 5/048 702/19 |
| 8,510,057 | B1 | 8/2013 | Avey et al. | |
| 8,543,339 | B2 | 9/2013 | Wojcicki et al. | |
| 8,589,437 | B1* | 11/2013 | Khomenko | G16B 50/00 707/783 |
| 8,645,343 | B2 | 2/2014 | Wong et al. | |
| 8,738,297 | B2 | 5/2014 | Sorenson et al. | |
| 8,786,603 | B2 | 7/2014 | Rasmussen et al. | |
| 8,855,935 | B2 | 10/2014 | Myres et al. | |
| 8,898,021 | B2* | 11/2014 | Perlin | C12Q 1/6851 702/19 |
| 8,990,250 | B1 | 3/2015 | Chowdry et al. | |
| 9,116,882 | B1 | 8/2015 | Macpherson et al. | |
| 9,213,944 | B1 | 12/2015 | Do et al. | |
| 9,213,947 | B1 | 12/2015 | Do et al. | |
| 9,218,451 | B2 | 12/2015 | Wong et al. | |
| 9,336,177 | B2 | 5/2016 | Hawthorne et al. | |
| 9,367,800 | B1 | 6/2016 | Do et al. | |
| 9,390,225 | B2 | 7/2016 | Barber et al. | |
| 9,405,818 | B2 | 8/2016 | Chowdry et al. | |
| 9,836,576 | B1 | 12/2017 | Do et al. | |
| 9,864,835 | B2 | 1/2018 | Avey et al. | |
| 10,432,640 | B1 | 10/2019 | Hawthorne et al. | |
| 10,516,670 | B2 | 12/2019 | Hawthorne et al. | |
| 2002/0019746 | A1* | 2/2002 | Rienhoff, Jr. | G06Q 50/22 705/2 |
| 2002/0095585 | A1 | 7/2002 | Scott | |
| 2002/0099789 | A1* | 7/2002 | Rudolph | G06F 16/40 709/217 |
| 2002/0133495 | A1 | 9/2002 | Rienhoff et al. | |
| 2002/0138572 | A1 | 9/2002 | Delany et al. | |
| 2002/0187496 | A1* | 12/2002 | Andersson | G16B 50/00 435/6.14 |
| 2004/0093334 | A1 | 5/2004 | Scherer | |
| 2005/0027560 | A1 | 2/2005 | Cook | |
| 2005/0152905 | A1* | 7/2005 | Omoigui | A61K 31/00 424/145.1 |
| 2005/0164704 | A1 | 7/2005 | Winsor | |
| 2007/0027917 | A1* | 2/2007 | Ariel | G06Q 10/109 |
| 2007/0166728 | A1* | 7/2007 | Abramson | G16B 45/00 435/6.11 |
| 2007/0198485 | A1* | 8/2007 | Ramer | G06F 16/9535 |
| 2007/0226250 | A1* | 9/2007 | Mueller | G06Q 10/087 |
| 2008/0009268 | A1* | 1/2008 | Ramer | H04L 67/2847 455/412.1 |
| 2008/0082955 | A1* | 4/2008 | Andreessen | G06F 16/958 717/100 |
| 2008/0131887 | A1* | 6/2008 | Stephan | G16B 20/00 435/6.11 |
| 2008/0162510 | A1 | 7/2008 | Baio et al. | |
| 2008/0228797 | A1* | 9/2008 | Kenedy | G16H 50/30 |
| 2009/0043752 | A1* | 2/2009 | Kenedy | G06Q 50/00 |
| 2009/0077110 | A1* | 3/2009 | Petri | G06F 16/2365 |
| 2009/0099789 | A1 | 4/2009 | Stephan et al. | |
| 2009/0112871 | A1 | 4/2009 | Hawthorne et al. | |
| 2009/0119083 | A1* | 5/2009 | Avey | G16B 45/00 703/11 |
| 2010/0042438 | A1* | 2/2010 | Moore | G06Q 50/24 705/3 |
| 2010/0070455 | A1* | 3/2010 | Halperin | G16B 20/00 706/54 |
| 2012/0270794 | A1 | 10/2012 | Eriksson et al. | |
| 2013/0345988 | A1 | 12/2013 | Avey et al. | |
| 2014/0006433 | A1 | 1/2014 | Hon et al. | |
| 2014/0067355 | A1 | 3/2014 | Noto et al. | |
| 2016/0026755 | A1 | 1/2016 | Byrnes et al. | |
| 2016/0103950 | A1 | 4/2016 | Myres et al. | |
| 2016/0171155 | A1 | 6/2016 | Do et al. | |
| 2016/0277408 | A1 | 9/2016 | Hawthorne et al. | |
| 2016/0350479 | A1 | 12/2016 | Han et al. | |
| 2017/0011042 | A1 | 1/2017 | Kermany et al. | |
| 2017/0017752 | A1 | 1/2017 | Noto et al. | |
| 2017/0220738 | A1 | 8/2017 | Barber et al. | |
| 2017/0228498 | A1 | 8/2017 | Hon et al. | |
| 2017/0277827 | A1 | 9/2017 | Granka et al. | |
| 2017/0277828 | A1 | 9/2017 | Avey et al. | |
| 2017/0329866 | A1 | 11/2017 | Macpherson | |
| 2017/0329891 | A1 | 11/2017 | Macpherson et al. | |
| 2017/0329899 | A1 | 11/2017 | Bryc et al. | |
| 2017/0329901 | A1 | 11/2017 | Chowdry et al. | |
| 2017/0329902 | A1 | 11/2017 | Bryc et al. | |
| 2017/0329904 | A1 | 11/2017 | Naughton et al. | |
| 2017/0329915 | A1 | 11/2017 | Kittredge et al. | |
| 2017/0329924 | A1 | 11/2017 | Macpherson et al. | |
| 2017/0330358 | A1 | 11/2017 | Macpherson et al. | |
| 2019/0281061 | A1 | 9/2019 | Hawthorne et al. | |

OTHER PUBLICATIONS

Preliminary Amendment dated Jul. 27, 2016 filed in U.S. Appl. No. 15/046,257.
U.S. Final Office Action dated Jun. 14, 2018 in U.S. Appl. No. 15/046,257.
U.S. Notice of Allowance dated Jul. 25, 2019 in U.S. Appl. No. 15/046,257.
U.S. Office Action dated Dec. 15, 2010 in U.S. Appl. No. 12/288,014.
U.S. Final Office Action dated Jul. 8, 2011 in U.S. Appl. No. 12/288,014.
U.S. Office Action dated May 9, 2012 in U.S. Appl. No. 12/288,014.
U.S. Final Office Action dated Oct. 5, 2012 in U.S. Appl. No. 12/288,014.
U.S. Office Action dated Sep. 13, 2013 in U.S. Appl. No. 12/288,014.
U.S. Final Office Action dated Feb. 27, 2014 in U.S. Appl. No. 12/288,014.
U.S. Office Action dated Jul. 29, 2015 in U.S. Appl. No. 12/288,014.
U.S. Notice of Allowance dated Nov. 24, 2015 in U.S. Appl. No. 12/288,014.
U.S. Notice of Allowance dated Jul. 22, 2019 in U.S. Appl. No. 16/420,063.
International Preliminary Report on Patentability dated Apr. 29, 2010 in Application No. PCT/US2008/011837.

(56) References Cited

OTHER PUBLICATIONS

International Search Report and Written Opinion dated Dec. 22, 2008 in PCT/US2008/11837.

* cited by examiner my health and traits
Age-related Macular Degeneration

Your Genetic Data

Show information for | Alex Wong ▼ | assuming | European ▼ | ethnicity and an age range of | 40-79 ▼
Alex Wong
Alex Wong
Greg Mendel (Dad)
Lilly Mendel (Mom)

Where's mine?

Alex Wong
4.8 out of 100 people of European ethnicity who share Alex Wong's genotype will get Age-related Macular Degeneration between the ages of 40 and 79.

} 4.8

Average
7.7 out of 100 people of European ethnicity will get Age-related Macular Degeneration between the ages of 40 and 79.

} 7.7

What does the Odds Calculator show me?

Use the ethnicity and age range selectors above to see the estimated incidence of Age-related Macular Degeneration due to genetics for someone with Alex Wong's genotype. The 23andMe Odds Calculator assumes that a person is free of the condition at the lower age in the range. You can use the name selector above to see the estimated incidence of Age-related Macular Degeneration for the genotypes of other people in your account.

The 23andMe Odds Calculator only takes into account effects of markers with known associations that are also on our genotyping chip. Keep in mind that aside from genetics, environment and lifestyle may also contribute to one's chances of developing late-stage AMD.

NOTE: Click here to read about recent changes to the Odds Calculator.

FIG. 1B my health and traits
Alcohol Flush Reaction

Alex Wong | help | log out

Your Genetic Data

| Who | Genotype | What It Means | Genes vs. Environment |
|---|---|---|---|
| Alex Wong | AA | No working copies of ALDH2. Extreme flushing reaction to alcohol. Highly unlikely to become dependent on alcohol. | Sensitivity to alcohol– the alcohol flush reaction– depends almost entirely on a person's genotype at two genes, ALDH2 and ADH1B. 23andMe currently reports your genotype at a SNP in ALDH2. It is possible that those with the AG or GG genotypes at the SNP are more sensitive to alcohol due to their genotype at ADH1B (which 23andMe does not report). |
|  | AG | One working copy of ALDH2 Moderate flushing reaction to alcohol. Somewhat less likely than average to become dependent on alcohol. | |
| Greg Mendel (Dad), Lilly Mendel (Mom) | GG | Two working copies of ALDH2 Little or no flushing reaction to alcohol. | |

FIG. 1C browse raw data

Alex Wong | help | log out

⬇ download raw data

Browsing SNPs on Chromosome 2: positions 19443 through 183882 out of 242951149

2
242M Bases
1886 Genes
48k SNPs

Jump to a gene: [____] [Go]  a SNP: [____] [Go]
or a chromosome:
[1][2][3][4][5][6][7][8][9][10][11][12][13][14][15][16][17][18][19][20][21][22][X][Y][MT]
« Return to your whole genome.

« Prev | Next «

| Gene | Position | SNP | Versions | Genotypes | |
|---|---|---|---|---|---|
| ⊞ LOC728944 | 19443 | rs4637157 | C or T | CT<br>CT<br>CT | Alex Wong<br>Greg Mendel (Dad)<br>Lilly Mendel (Mom) |
| ⊞ LOC728944 | 23012 | rs13423995 | A or G | AG<br>AA<br>AA | Alex Wong<br>Greg Mendel (Dad)<br>Lilly Mendel (Mom) |
| ⊞ LOC728944 | 26787 | rs11900053 | C or T | CT<br>CT<br>CT | Alex Wong<br>Greg Mendel (Dad)<br>Lilly Mendel (Mom) |
| ⊞ LOC728944 | 28938 | rs11542478 | A or C | AA<br>AA<br>AA | Alex Wong<br>Greg Mendel (Dad)<br>Lilly Mendel (Mom) |
| ⊞ LOC728944 | 37808 | rs11897072 | A or G | GG<br>AG<br>AG | Alex Wong<br>Greg Mendel (Dad)<br>Lilly Mendel (Mom) |
| ⊞ LOC727737 | 75793 | rs6713375 | C or T | TT<br>TT<br>TT | Alex Wong<br>Greg Mendel (Dad)<br>Lilly Mendel (Mom) |
| ⊞ LOC727737 | 79910 | rs300789 | A or G | AA<br>AA<br>AA | Alex Wong<br>Greg Mendel (Dad)<br>Lilly Mendel (Mom) |
| ⊞ LOC727761 | 94979 | rs7588043 | C or T | CT<br>CT<br>CC | Alex Wong<br>Greg Mendel (Dad)<br>Lilly Mendel (Mom) |
| ⊞ LOC727761 | 96692 | rs6755432 | C or T | CT<br>CT<br>TT | Alex Wong<br>Greg Mendel (Dad)<br>Lilly Mendel (Mom) |
| ⊞ LOC727761 | 100819 | rs300780 | C or T | CT<br>CT<br>TT | Alex Wong<br>Greg Mendel (Dad)<br>Lilly Mendel (Mom) |
| ⊞ *intergenic* | 105035 | rs300773 | C or T | TT<br>TT<br>TT | Alex Wong<br>Greg Mendel (Dad)<br>Lilly Mendel (Mom) |

FIG. 1D

Invite People to Share Genomes close or Esc Key

To share with friends or family, ask or search for their 23andMe usernames and enter them below. What will I be sharing?

Username: [_____] ⟵ 502

*To invite multiple people at once, add commas between usernames.*

Profiles: ☑ Ian Mendel

Level: ● Basic   ○ Complete

Message text: [ Let's share our profiles on 23andMe and compare our genomes. ]

*Maximum message length is 500 characters.*

[ invite ]

FIG. 5

Account Records 1101

| ACCOUNT ID | ACCOUNT USERNAME | PASSWORD | ACCOUNT NAME | ACCOUNT EMAIL ADDRESS | SHIPPING ADDRESS |
|---|---|---|---|---|---|
| 50001 | familydoe | password_x | The Doe Family | john@doe.com | 5 Market St., San Francisco, CA 94132 |
| 50002 | boblee | password_y | Bob Lee | bob@lee.com | P.O. Box 8, New York, NY 10027 |
| ... | | | | | |

Profile Records 1102

| PROFILE ID | ACCOUNT ID | PROFILE NAME | PROFILE EMAIL ADDRESS | BIRTHDATE | BIRTHPLACE | CURRENT LOCATION | ANCESTRY |
|---|---|---|---|---|---|---|---|
| 10001 | 50001 | John Doe | john@doe.com | 11/15/1975 | San Francisco | San Francisco | European |
| 10002 | 50001 | Mary Doe | mary@doe.com | 9/7/1977 | Los Angeles | San Francisco | European |
| 10003 | 50002 | Bob Lee | bob@lee.com | 2/4/1968 | New York | New York | Asian |
| ... | | | | | | | |

FIG. 11A

Phenotype Records 1104

| PHENOTYPE ID | HEIGHT | WEIGHT | EYE COLOR | HAIR COLOR | ... |
|---|---|---|---|---|---|
| 20001 | 5'5" | 120 lb | Blue | Brown | |
| 20002 | | | | | |
| 20003 | 5'10" | 170 lb | Brown | Brown | |
| 20004 | | | | | |
| 20005 | | | | | |
| ... | | | | | |

Genotype Records 1106

| GENOTYPE ID | SNP DATA | TEST RESULT 1 | TEST RESULT 2 | ... |
|---|---|---|---|---|
| 30001 | | Yes | | |
| 30002 | | No | | |
| 30003 | SNP_x | No | 0.8 | |
| 30004 | SNP_y | Yes | 0.14 | |
| ... | | | | |

FIG. 11B

Sharing Table 1200

| ACCOUNT SHARED TO | PROFILE SHARED FROM | SHARING LEVEL |
|---|---|---|
| 50002 | 10001 | Basic |
| 50002 | 10002 | Extended |
| . . . | . . . | . . . |
| | | |

FIG. 12

GENOME SHARING

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND OF THE INVENTION

Recently, interest in genetics and genetic testing has risen as increasing amounts of research show how an individual's genetic information can influence aspects of a person's ancestry, appearance, behavior, and physiology. Genetic information can be made available to an individual via the Internet. To prevent others from viewing personal data, the individual is typically required to login using a password in order to gain access to his data. In some cases, an individual may wish to share his personal data with one or more other individuals, such as family members. However, current techniques for sharing personal data are basic and have limited capability. As such, improvements in the sharing of personal data would be useful.

BRIEF DESCRIPTION OF THE DRAWINGS

Various embodiments of the invention are disclosed in the following detailed description and the accompanying drawings.

FIGS. 1B-1D illustrate examples embodiments of interfaces for displaying genetic data from multiple users.

FIG. 5 is a diagram illustrating an example of an interface for a sharing invitation.

FIGS. 11A-11B are diagrams illustrating an embodiment of records in various databases in a system for sharing genetic or other data.

FIG. 12 is a diagram illustrating an embodiment of a sharing table.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1A:
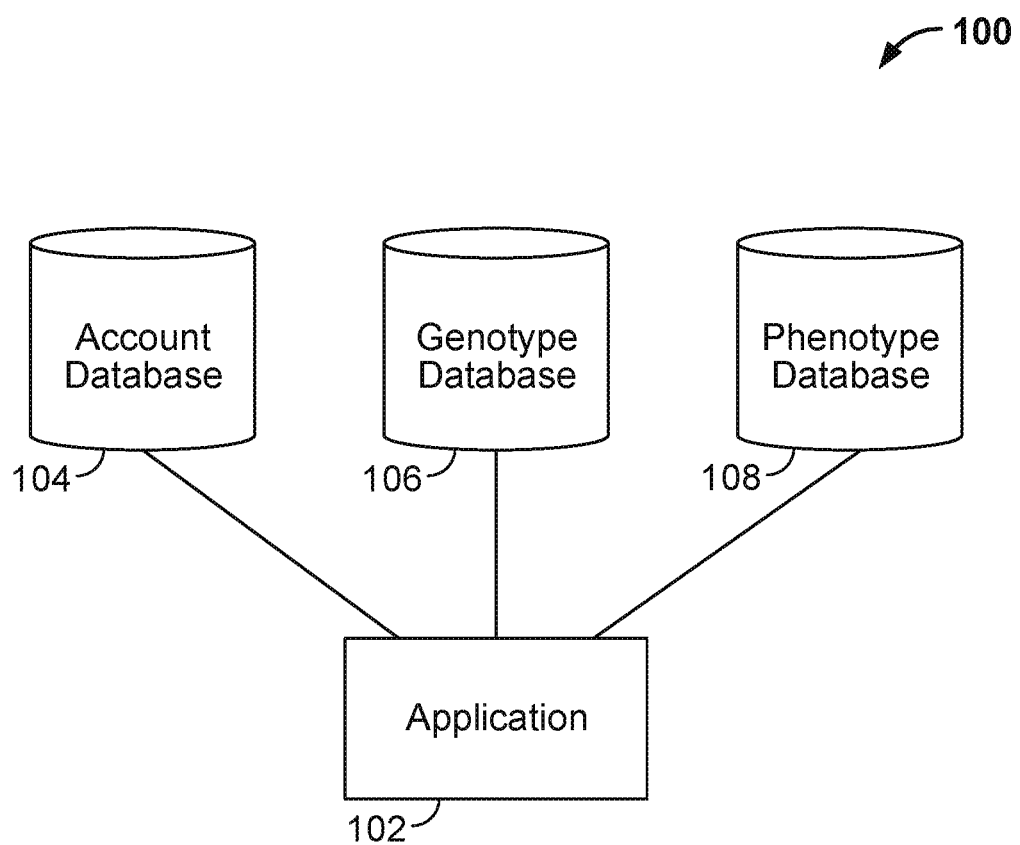
FIG. 1A is a block diagram illustrating an embodiment of a system for sharing genetic or other data.

FIG. 1A is a block diagram illustrating an embodiment of a system for sharing genetic or other data. In the example shown, system 100 is shown to include application 102, account database 104, genotype database 106 and phenotype database 108. Application 102 interacts with account database 104, genotype database 106 and phenotype database 108 to access data associated with an individual. Account database 104 contains identifying data associated with individuals, such as names, addresses, etc. Genotype database 106 contains data associated with the individuals' genetics, such as single nucleotide polymorphism (SNP) data, including calls for various SNPs or genetic test results. Phenotype database 108 includes data associated with the individuals' phenotypes, such as hair color, eye color, birth date, or medical conditions. Phenotype data can be obtained based on user survey(s) or other interactive tools. A phenotype includes any observable characteristic of an organism, such as its morphology, development, biochemical or physiological properties, or behavior. Phenotypes are influenced by a combination of genetic and environmental factors.

In some embodiments, application 102 is a web application that is part of a website that allows individuals to view their genetic and other personal data. An example of such a website is www.23andme.com. An individual may use such a website to ascertain descriptions of certain traits he has and the genes associated with them. For example, the website www.23andme.com provides an odds calculator that can combine genetic and phenotypic information, age, and ethnicity to get an idea of which common health concerns are most likely to affect the individual. Such an odds calculator may be used by an individual to determine information for an individual such as his likelihood of developing type 2 diabetes. Additionally, such a website may allow an individual to determine if he has a particular gene, such as the one that allows for tasting the bitter flavor of broccoli.

In some embodiments, application 102 allows an individual to share at least a subset of his genetic and other personal data with other users. FIGS. 1B-1D illustrate examples embodiments of interfaces for displaying genetic data from multiple users. For example, in FIGS. 1B-1C, a user may view descriptions of traits or odds associated with different health concerns associated with other individuals. In another example, FIG. 1D, a "Genome Browser" interface allows a user to view his raw genome data and the raw genome data of other individuals with which sharing of raw genome data has been established. In some embodiments, the raw genome data for multiple individuals are displayed together.

Although databases, records, fields, rows, and columns may be described herein, in various embodiments, any appropriate technique for storing data may be used. A database is an example of a set of stored data. In various embodiments, any appropriate set of stored data may be used besides a database. A set of stored data may include a data repository or data store, such as a database or a file. A set of stored data may include one or more data structures, such as records, rows, or objects.

Figure 2:
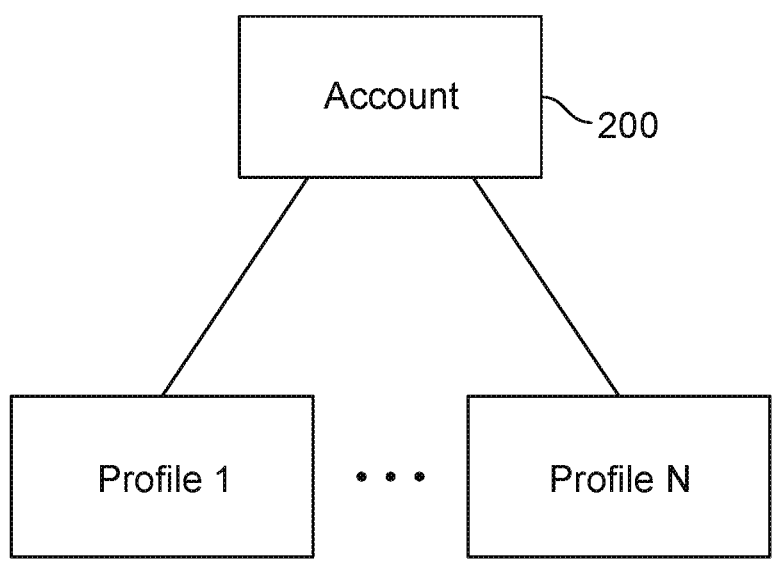
FIG. 2 is a block diagram illustrating an embodiment of an account in a web application that allows sharing of personal data.

FIG. 2 is a block diagram illustrating an embodiment of an account in a web application that allows sharing of personal data. In some embodiments, account 200 is stored in account database 104. In the example shown, an individual (e.g., John Doe) signs up for an account 200 in the web application by specifying a username, password, security question, and birth date. In some embodiments, terms of service (TOS) are displayed and a user must agree to the TOS in order to sign up for an account. In order to access the account in the web application, the username and password must be specified. An account can own 0 or more profiles. Each profile is associated with a different individual or human being. For example, profiles 1-3 might be for John Doe, Mary Doe (his wife), and Bobby Doe (his son), respectively. In the example shown, N profiles are owned by account 200. Stated another way, account 200 owns N profiles. In some embodiments, anyone with access to account 200 has read and/or write access to (i.e., is able to or has permission to view and/or modify) any of profiles 1-N. In some embodiments, profiles 1-N each contain data associated with an individual, such as name and birthdate, and account 200 contains data that is not specific to an individual, such as an account name (e.g., The Doe Family), an account username (e.g., doefamily) and password.

In some embodiments, a profile may be transferred from one account to another. For example, Mary Doe divorces John Doe and would like to set up her own account to own her profile. As another example, Bobby Doe grows up (e.g., turns 18) and would like to have his profile owned by his own account. In some embodiments, a profile can only be owned by one account, so once Mary Doe's profile is owned by Mary Doe's account, then it is no longer owned by John Doe's account. In some embodiments, a user logs into the doefamily account to request the transfer and a user logs into Mary Doe's account to accept the transfer. In some embodiments, when the user of the doefamily account requests the transfer, the user must provide a password associated with the destination account and/or answer a secret question.

Figure 3:
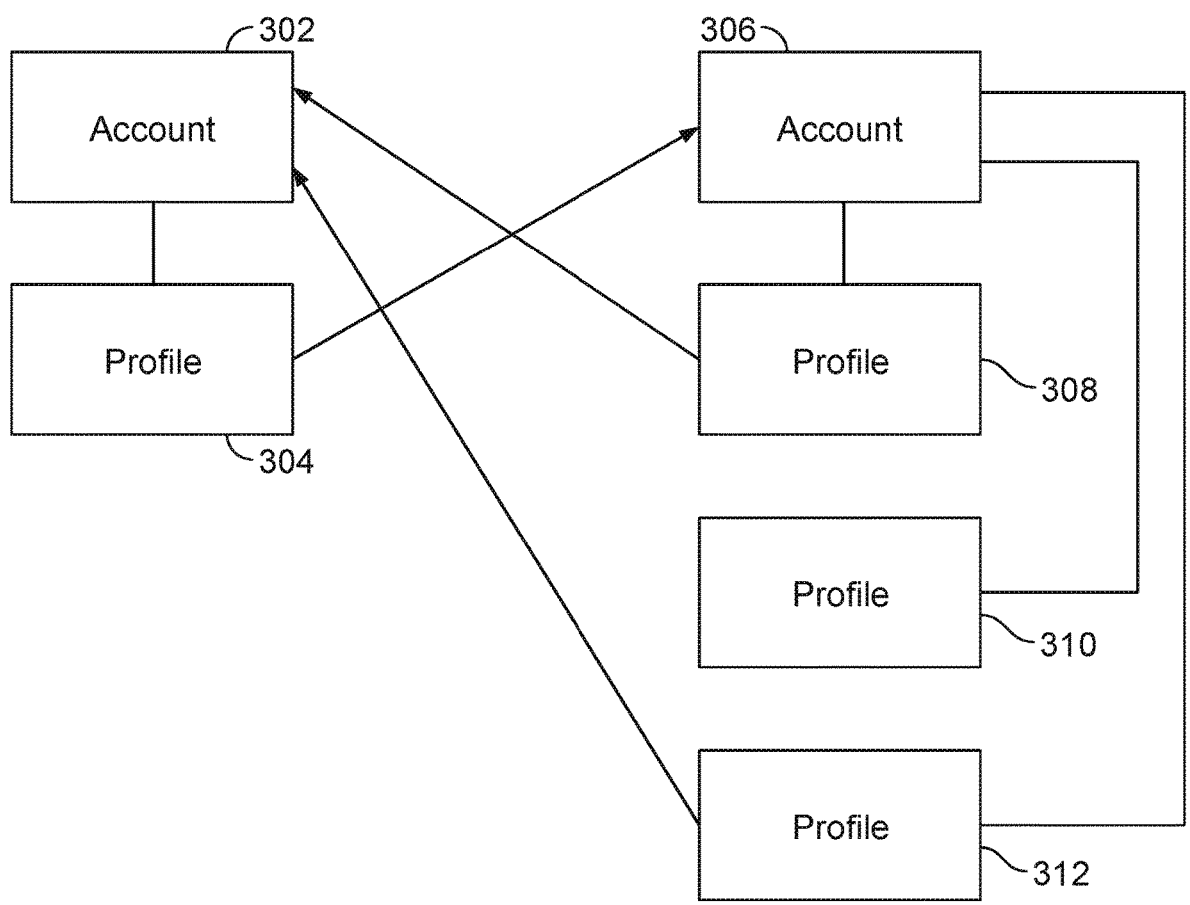
FIG. 3 is a block diagram illustrating an embodiment of sharing of personal data.

FIG. 3 is a block diagram illustrating an embodiment of sharing of personal data. In the example shown, account 302 owns profile 304 and account 306 owns profiles 308, 310, and 312. Profiles 308 and 312 are shared with or "shared to" account 302. Stated another way, sharing has been established from profiles 308 and 312 to account 302. In other words, account 302 has read access to (e.g., is able to or has permission to view) at least a subset of data associated with profiles 308 and 312.

Profile 304 is shared with or "shared to" account 306. Stated another way, sharing has been established from profile 304 to account 306. In other words, account 306 has read access to at least a subset of data associated with profile 304. In some embodiments, certain data associated with a profile is public data; that is, any other account has read access to public data. In such embodiments, when a profile is shared to an account, it means that the account has read access to at least a subset of nonpublic data associated with the profile.

Figure 4:
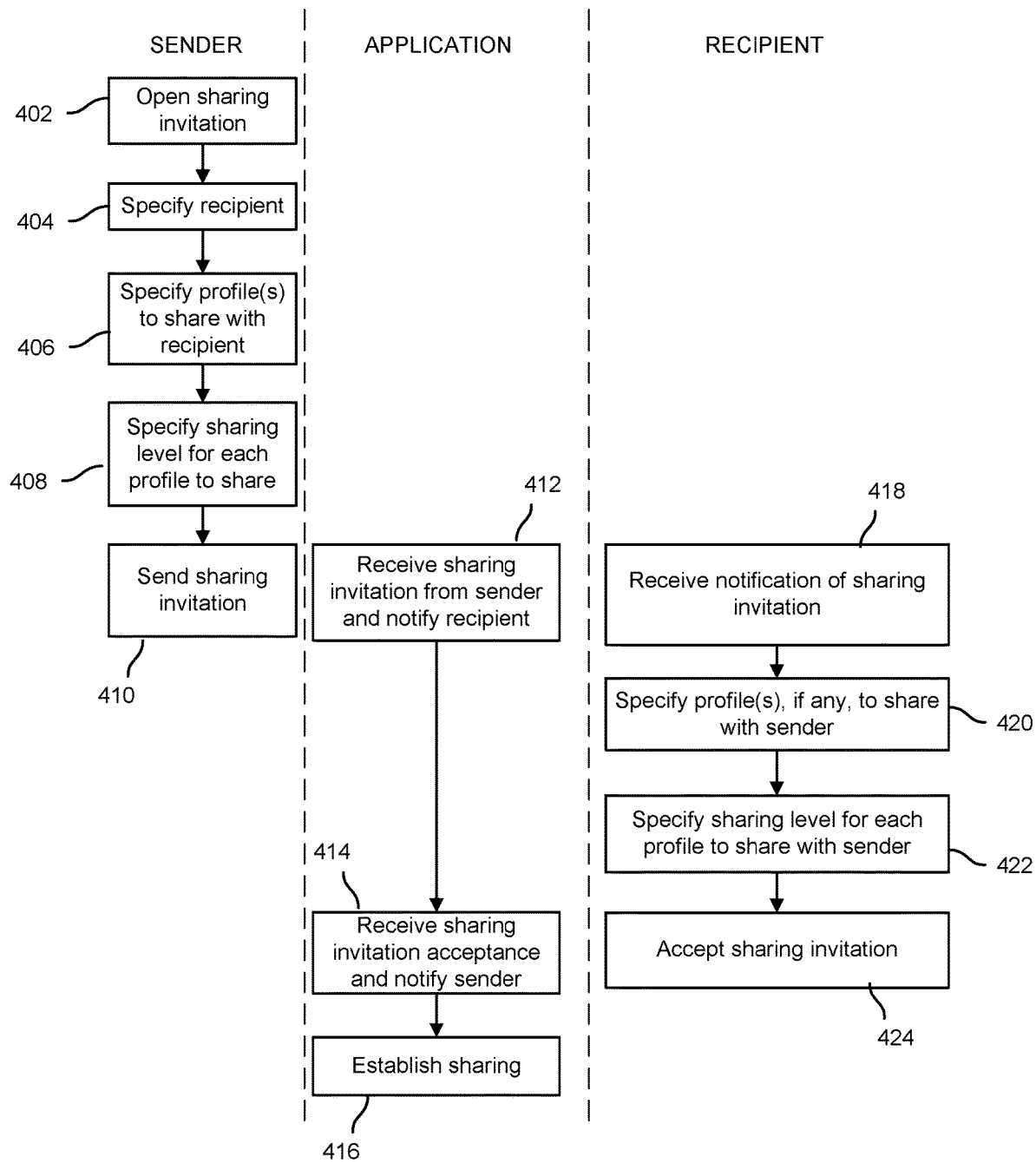
FIG. 4 is a flow chart illustrating an embodiment of a process for initiating and establishing sharing.

FIG. 4 is a flow chart illustrating an embodiment of a process for initiating and establishing sharing. In some embodiments, process 400 or at least steps 412-416 are performed by application 102. In some embodiments, steps 402-410 are associated with a first account. For example, a user of the first account causes steps 402-410 to be performed. In some embodiments, steps 418-424 are associated with a second account. For example, a user of the second account causes steps 418-424 to be performed.

In the example shown, at 402, a sharing invitation is opened. For example, a user logs into a first account and then opens an interface for a sharing invitation. FIG. 5 is a diagram illustrating an example of an interface for a sharing invitation.

At 404, a recipient is specified. For example, the interface may provide a place to enter a recipient. In FIG. 5, the user can enter or search for usernames using box 502. In some embodiments, an account user can specify that the account username (e.g., doefamily) and/or account name (e.g., The Doe Family) is searchable. In some embodiments, names and/or email addresses associated with profiles (e.g., John Doe, Mary Doe, and/or Bobby Doe) may be searchable. In some embodiments, the user can search based on other information, such as Current Location, type 1 diabetes risk, etc. In some embodiments, in order for data to be searchable, the data must be made public.

In some embodiments, 404 is performed before 402. For example, a user's profile may be publicly represented on the website. For example, if a user has posted a message in a community thread, his or her profile picture and public nickname will be displayed in that thread. Another user may click on the picture or nickname to view the posting user's profile page. From this page, the other user may initiate a sharing invitation by clicking on an invitation link. In this case, the inviting user does not need to specify the invitee again in the invitation, as it is inherited from the profile page on which the invitation link was clicked. An invitation link may also be found next to the posting user's picture and nickname, in which case the inviting user can click directly on that link to invite without first going to the invitee's profile page.

Alternatively, a user's profile may be found and an invitation sent to them through user search results.

At 406, profile(s) to share with the recipient are specified. For example, the profiles for John Doe and Mary Doe may be specified. Then the profile for Bobby Doe will not be shared. In FIG. 5, the profile Ian Mendel is the only profile associated with the account and it is selected as the profile to share. In some embodiments, if there is only one profile associated with the account, this step is skipped and the one profile is selected by default. In some embodiments, the sender can select no profiles to share with the recipient.

At 408, a sharing level for each profile to share is specified. A sharing level indicates a subset of data associated with the profile to share or to which to provide read access. A sharing level may be embodied in various ways. Specific data to share may be individually indicated, or groups of data to be shared may be indicated. In FIG. 5, two sharing levels may be indicated: "Basic" or "Complete". When "Basic" is selected, then a smaller subset of data is shared than when "Complete" is selected. For example, "Basic" might include ancestry and general comparison features, while "Complete" might include detailed health and traits articles and odds calculations, or full SNP-level information in the form of a genome browser. In some embodiments, a sharing level to request from the other account holder is also specified. The user may also request certain profiles from other account. In some embodiments, the sharing level is implicitly symmetric, so that the sharing level from the sender to the recipient is the same as the sharing level from the recipient to the sender. The sender may also attach a personal message to the invitation.

At 410, the sharing invitation is sent. For example, in FIG. 5, the "invite" button is selected. In some embodiments, the sharing invitation includes the sharing levels specified at 408.

At 412, the sharing invitation is received from the sender and the recipient is notified. For example, the web application is notified that the sharing invitation was sent and sends an email to the recipient.

At 418, a notification of the sharing invitation is received. For example, the recipient receives an email message notifying him that a sharing invitation has been received and to login to his account to respond to it.

Figure 6:
FIG. 6 is a diagram illustrating an example of an interface for responding to a sharing invitation.

At 420, profile(s) to share with the sender, if any, are specified. For example, the recipient logs into his account and an interface is presented for responding to the invitation. FIG. 6 is a diagram illustrating an example of an interface for responding to a sharing invitation. In this example, Alex Wong is the sender of the invitation and has requested sharing level Basic. The recipient can select one or more profiles to share back with the sender. In some embodiments, the recipient can select no profiles to share back with the sender. In some embodiments, if there is only one profile associated with the account, this step is skipped and the one profile is selected by default.

At 422, a sharing level for each profile to share back with the sender is specified. In some embodiments, the recipient can specify a sharing level (e.g., Basic or Complete) for each profile to be shared back. (In FIG. 6, this option is not available.)

At 424, the sharing invitation is accepted. For example, in FIG. 6, the "OK" button is selected.

At 414, the sharing invitation acceptance is received from the recipient and the sender is notified. For example, the web application is notified that the sharing invitation was accepted and sends an email to the recipient.

At 416, sharing is established. In some embodiments, before sharing can be established, the sender reconfirms the request by logging into the sender's account and reconfirming the request. In some cases, the sender may decide not to reconfirm the request, if, for example, at 420, the sender does not recognize the recipient, who may be a hacker.

In some embodiments, each account only has one profile, so steps 406 and 420 are skipped. In some embodiments, sharing levels are preset and steps 408 and 422 are skipped. In some embodiments, the sharing levels are bidirectional (the same in both directions) so that whatever sharing level is specified at 408 is automatically the sharing level specified at 422. Thus, step 422 may be skipped and the sharing level preset to the sharing level specified at 408.

Once sharing is established, sharing levels may change, sharing may be terminated, etc. In some embodiments, sharing is unilaterally stopped. In other words, when the sharing of a first account's profile to a second account is terminated, then sharing from the second account's profile to the first account is automatically terminated. In some embodiments, either party can terminate sharing. In some embodiments, one or more levels of sharing may be upgraded and/or downgraded.

Figure 7:
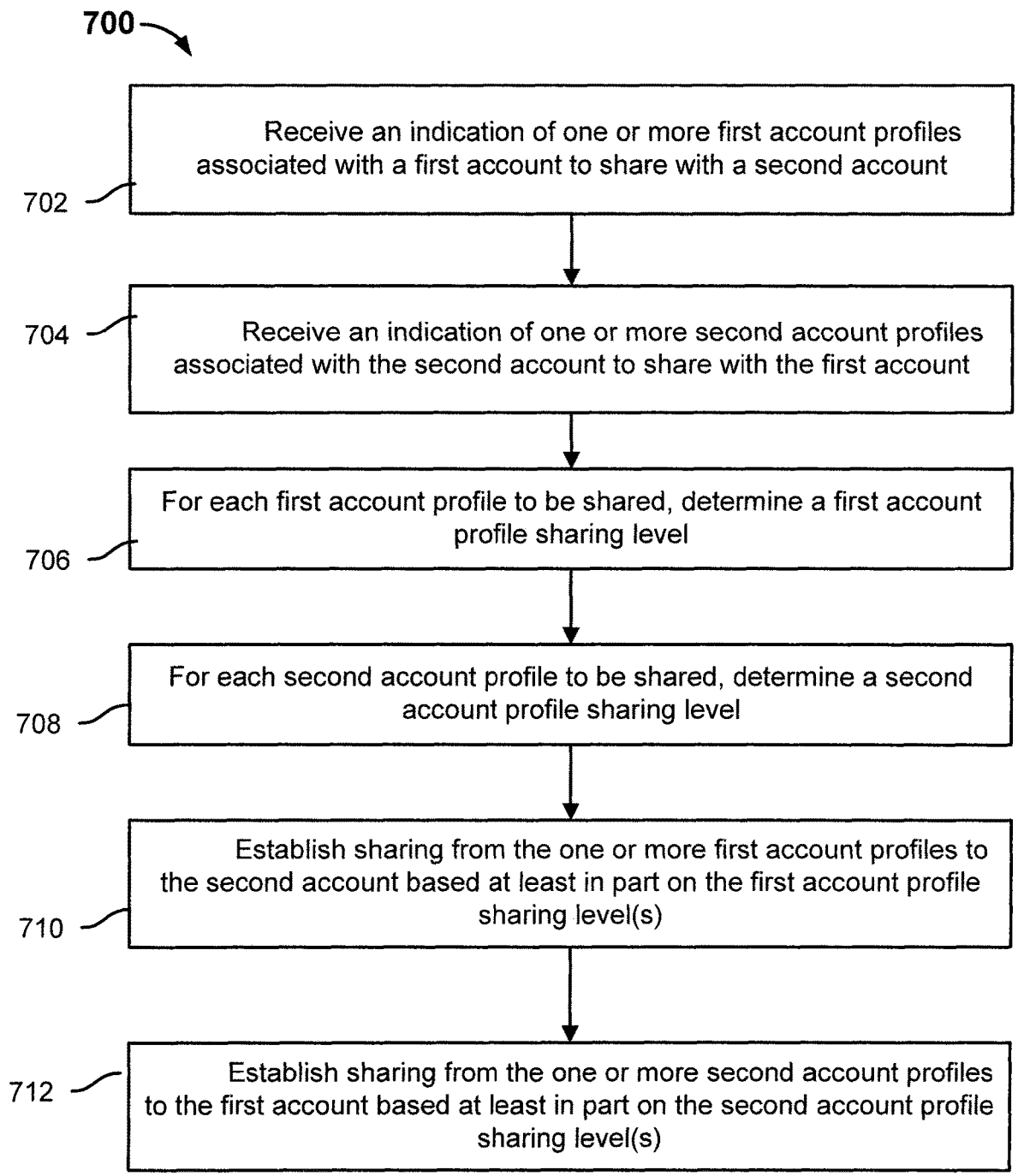
FIG. 7 is a flow chart illustrating an embodiment of a process for establishing sharing.

FIG. 7 is a flow chart illustrating an embodiment of a process for establishing sharing. In some embodiments, process 700 is used to perform steps 412-416. In the example shown, at 702, an indication of one or more first account profiles associated with a first account to share with a second account is received. For example, if a user is providing information as in FIG. 4, the profile(s) specified at 406 are received. At 704, an indication of one or more second account profiles associated with the second account to share with the first account is received. For example, the profile(s) specified at 420 are received. At 706, for each first account profile to be shared, a first account sharing level is determined. For example, the sharing level(s) specified at 408 are determined. At 708, for each second account profile to be shared, a second account sharing level is determined. For example, the sharing level(s) specified at 422 are determined. At 710, sharing is established from the one or more first account profiles to the second account based at least in part on the first account profile sharing level(s). At 712, sharing from the one or more second account profiles to the first account is established based at least in part on the second account profile sharing level(s). In some embodiments, steps 702-708 result from what a user specifies in a web interface to a web application.

Figure 8:
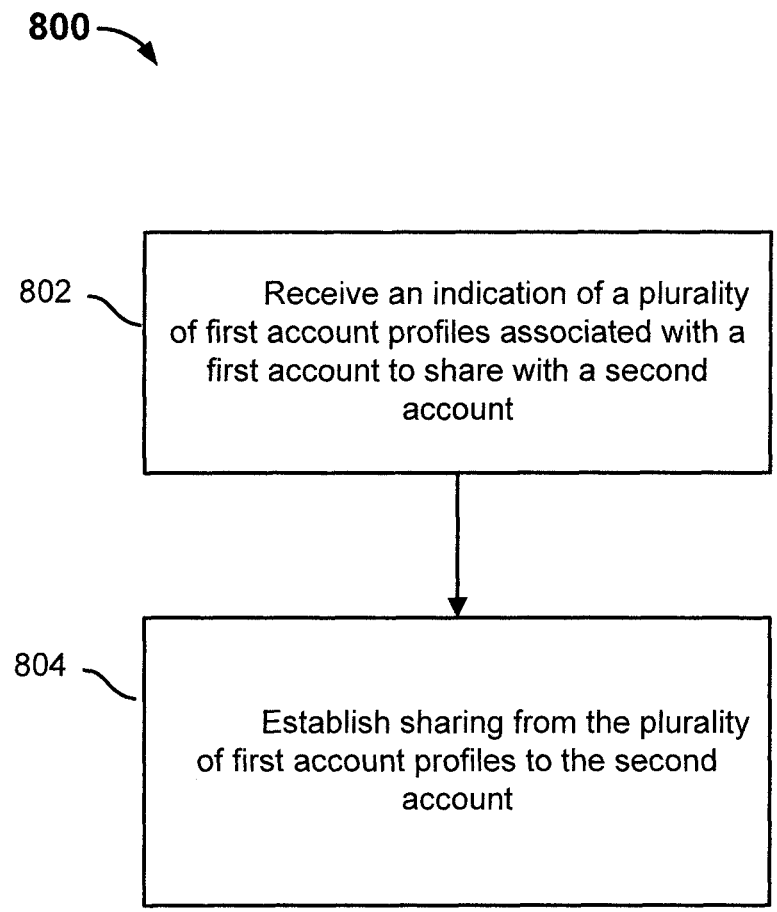
FIG. 8 is a flow chart illustrating an embodiment of a process for establishing sharing of multiple profiles.

FIG. 8 is a flow chart illustrating an embodiment of a process for establishing sharing of multiple profiles. In some embodiments, process 800 is used to perform steps 412-416. In the example shown, at 802, an indication of a plurality of first account profiles associated with a first account to share with a second account is received. At 804, sharing from the plurality of first account profiles to the second account is established. Sharing comprises the second account having read access to a subset of nonpublic data associated with the plurality of first account profiles.

Figure 9:
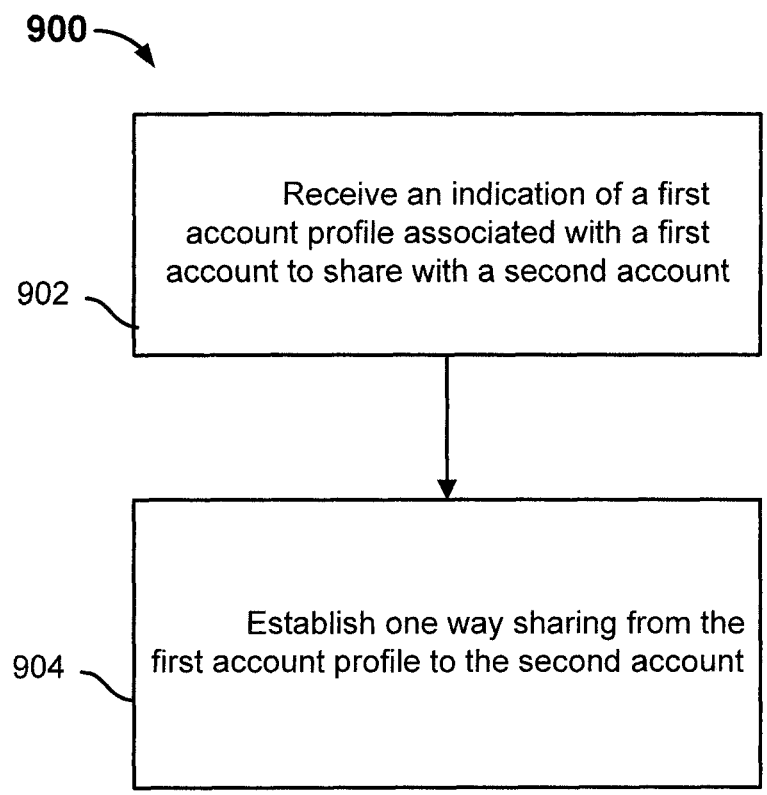
FIG. 9 is a flow chart illustrating an embodiment of a process of establishing one way or unidirectional sharing.

FIG. 9 is a flow chart illustrating an embodiment of a process of establishing one way or unidirectional sharing. In some embodiments, process 900 is used to perform steps 412-416. In the example shown, at 902, an indication of a first account profile associated with a first account to share with a second account is received. At 904, one way sharing from the first account profile to the second account is established. One way sharing means that the second account has read access to a subset of nonpublic data associated with the first account profile, but the first account does not have read access to nonpublic data associated with the second account. For example, an individual may share the individual's data with a doctor, but the doctor does not need to share the doctor's data back to the individual.

Figure 10:
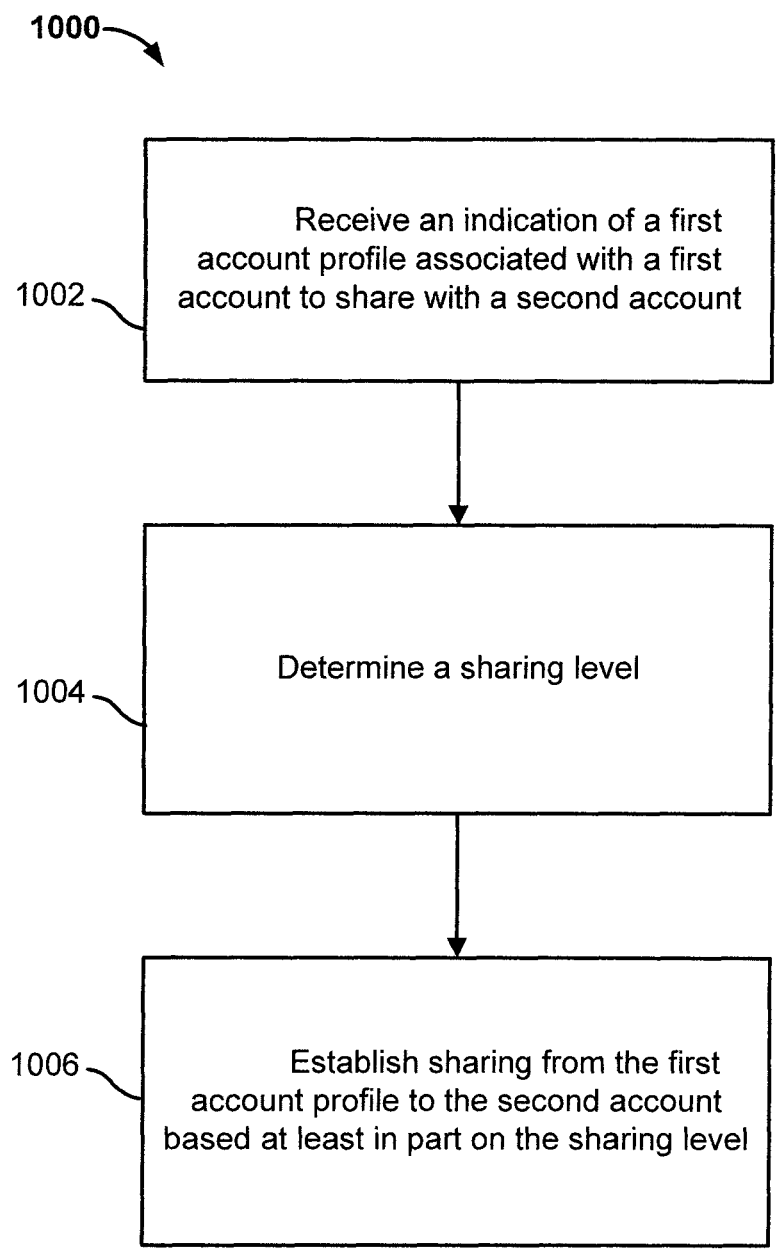
FIG. 10 is a flow chart illustrating an embodiment of a process for establishing sharing using sharing level(s).

FIG. 10 is a flow chart illustrating an embodiment of a process for establishing sharing using sharing level(s). In some embodiments, process 1000 is used to perform step 416. In the example shown, at 1002, an indication of a first account profile associated with a first account to share with a second account is received. At 1004, a sharing level is determined. In some embodiments, the sharing level indicates a subset of data associated with the first account profile to share with the second account. At 1006, sharing from the first account profile to the second account is established based at least in part on the sharing level. In some embodiments, sharing comprises the second account having read access to the subset of data indicated by the sharing level.

FIGS. 11A-11B are diagrams illustrating an embodiment of records in various databases in a system for sharing genetic or other data. In the example shown, account records 1101 and profile records 1102 are stored in an account database, such as account database 104. Phenotype records 1104 are stored in a phenotype database, such as phenotype database 108. Genotype records 1106 are stored in a genotype database, such as genotype database 108.

Referring to FIG. 2, in some embodiments, each account record 1101 is an example of account 200 and each profile record 1102 is an example of one of profiles 1-N.

In the example shown, each account record includes: "Account ID", "Account Username", "Password", "Account Name", "Account Email Address", and "Shipping Address". In some embodiments, "Account ID" uniquely identifies each account record. In some embodiments, the "Password" is encrypted using a hash function.

In some embodiments, profile records 1102 include data that can be used to identify an individual. In some embodiments, each profile record 1102 is associated with a different individual. An individual can be a person or in some embodiments, an animal, such as a pet. Each profile record includes: "Profile ID", "Account ID", "Profile Name", "Profile Email Address", "Birthdate", "Birthplace", "Current Location", and "Ancestry". In some embodiments, "Profile ID" uniquely identifies each profile record.

An account may own or be associated with one or more profile records. In profile records 1102, "Account ID" indicates the account that owns or is associated with each profile record. As shown, multiple profile records may have the same "Account ID" or be associated with the same account. When a profile is transferred from one account to another account, the "Account ID" of the profile is updated to the new account's "Account ID".

In some embodiments, account records contain data that is not specific to an individual. In some embodiments, profile records contain data associated with an individual. In some embodiments, each account record also includes a "Profiles" field. "Profiles" includes the Profile IDs of the profile records associated with the account.

Referring to FIG. 11B, in the example shown, each phenotype record includes: "Phenotype ID", "Height", "Weight", "Eye Color", and "Hair Color". Other examples of fields that may be included in a phenotype record include medical conditions, such as whether the individual has type 1 diabetes, survey answers, or data collected from interactive tools. In some embodiments, phenotype records 1104 include data associated with the phenotype of an individual. In some embodiments, "Phenotype ID" uniquely identifies each phenotype record.

In the example shown, each genotype record includes: "Genotype ID", "SNP Data", "Test Result 1", and "Test Result 2". In some embodiments, "SNP Data" includes calls for various SNPs and confidence values for the calls for the individual. "Test Result 1" and "Test Result 2" could be results of a genetic test, such as whether the individual can taste bitterness in broccoli, or the individual's type 1 diabetes risk. In some embodiments, "Genotype ID" uniquely identifies each genotype record.

In some embodiments, an application such as application 102 retrieves profile records, phenotype records, and genotype records as needed in order to provide genetic or other data to users over the Internet.

In some embodiments, some of the fields shown in profile records 1102 are stored in separate records in a separate database. For example, the "Birthdate", "Birthplace", and "Ancestry" fields could be stored in biographical records in a biographical database. The biographical records might also include a social security number. This way, should a hacker obtain access to the profile records, he could not determine which profile records belong to which biographical records. This may be useful to address concerns of identity theft.

FIG. 12 is a diagram illustrating an embodiment of a sharing table. In some embodiments, a sharing table is used to store sharing information from the various profiles to the various accounts in system 100. In the example shown, sharing table 1200 includes three columns: "Account Shared To", "Profile Shared From", and "Sharing Level". The first row of sharing table 1200 indicates that the profile 10001 is shared to the account 50002 at a basic sharing level. As shown in FIG. 11A, profile 10001 is associated with account 50001 having username familydoe. Account 50002 is associated with username boblee. Thus, a user of account 50001 has allowed users of account 50002 read access to a subset of nonpublic data in profile 10001. The subset is specified by the sharing level, in this case Basic. In some embodiments, the Basic sharing level means there is read access to a basic subset of nonpublic data and the Extended sharing level means there is read access to an extended subset of nonpublic data, wherein the extended subset is a superset of the basic subset.

In some embodiments, there are three or more sharing levels available. In some embodiments, the level of sharing can be individually configured at a lower level of granularity. For example, a user may specifically select which data to which to allow read access.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for sharing genetic data, comprising:
providing an account database comprising records for a plurality of users of an application and a genotype database comprising genotype records associated with the plurality of users;
receiving, from a first account, a request to share nonpublic information with a second account through the application, wherein:
the first account is associated with a first user and one or more first user genotype records,
the one or more first user genotype records are stored in the genotype database, are uniquely associated with the first account of the first user and comprise genotype information of the first user,
the second account is associated with a second user and one or more second user genotype records,
the one or more second user genotype records are stored in the genotype database, are uniquely associated with the second account of the second user and comprise genotype information of the second user;
in response to receiving the request from the first account, notifying the second account of the request from the first account;
in response to notifying the second account of the request from the first account, receiving, from the second account, an acceptance of the request to share nonpublic information through the application; and
in response to receiving, from the second account, the acceptance of the request, establishing sharing of nonpublic information associated with the first account to the second account and sharing of non-public information associated with the second account to the first account.

2. The method of claim 1, wherein the non-public information associated with a user comprises information related to health of the user.

3. The method of claim 1, wherein the non-public information associated with an account comprises information about a likelihood of one or more health concerns to affect the user associated with the account.

4. The method of claim 1, wherein the non-public information associated with an account comprises information about a risk of developing a health-related condition.

5. The method of claim 1, wherein the non-public information associated with an account comprises health information associated with the genome of the first user.

6. The method of claim 1, wherein the non-public information associated with an account comprises single nucleotide polymorphism (SNP) data of the user associated with the account.

7. The method of claim 1, wherein the non-public information associated with an account comprises information about one or more traits associated with the genotype information of the user associated with the account.

8. The method of claim 7, wherein the one or more traits comprise a trait related to taste sensitivity.

9. The method of claim 8, wherein the trait related to taste sensitivity is a trait related to bitterness sensitivity.

10. The method of claim 1, wherein the non-public information associated with an account comprises phenotype information of the user associated with the account.

11. The method of claim 1, wherein the non-public information associated with an account comprises genotype information of the user associated with the account.

12. The method of claim 1, wherein the non-public information associated with an account comprises information about a particular gene of the user associated with the account.

13. The method of claim 1, wherein the non-public information associated with an account comprises ancestry information of the user associated with the account.

14. The method of claim 1, wherein the application is a web application.

15. The method of claim 1, further comprising, receiving from the first user, an indication of a subset of non-public information to be shared.

16. The method of claim 1, wherein the same level of information is shared from the first account to the second account as is shared from the second account to the first account.

17. A system for sharing genetic data, comprising:
an account database comprising records for a plurality of users of an application;
a genotype database comprising genotype records associated with the plurality of users; and
one or more processors configured to:
receive, from a first account, a request to share non-public data with a second account through the application, wherein:
the first account is associated with a first user and one or more first user genotype records,
the one or more first user genotype records are stored in the genotype database, are uniquely associated with the first account of the first user and comprise genotype information of the first user,
the second account is associated with a second user and one or more second user genotype records,
the one or more second user genotype records are stored in the genotype database, are uniquely associated with the second account of the second user and comprise genotype information of the second user;
in response to receiving the request from the first account, notify the second account of the request from the first account;
in response to notifying the second account of the request from the first account, receive, from the second account, an acceptance of the request to share non-public data through the application; and
in response to receiving, from the second account, the acceptance of the request, establish sharing of non-public information associated with the first account to the second account and sharing of non-public information associated with the second account to the first account.

18. The system of claim 17, wherein the non-public information associated with a user comprises information related to health of the user.

19. The system of claim 17, wherein the non-public information associated with an account comprises information about a likelihood of one or more health concerns to affect the user associated with the account.

20. The system of claim 17, wherein the non-public information associated with an account comprises information about a risk of developing a health-related condition.

21. The system of claim 17, wherein the non-public information associated with an account comprises health information associated with the genome of the first user.

22. The system of claim 17, wherein the non-public information associated with an account comprises single nucleotide polymorphism (SNP) data of the user associated with the account.

23. The system of claim 17, wherein the non-public information associated with an account comprises information about one or more traits associated with the genotype information of the user associated with the account.

24. The system of claim 23, wherein the one or more traits comprise a trait related to taste sensitivity.

25. The system of claim 24, wherein the trait related to taste sensitivity is a trait related to bitterness sensitivity.

26. The system of claim 17, wherein the non-public information associated with an account comprises phenotype information of the user associated with the account.

27. The system of claim 17, wherein the non-public information associated with an account comprises information about a particular gene of the user associated with the account.

28. The system of claim 17, wherein the information the non-public information associated with an account comprises ancestry information of the user associated with the account.

29. The system of claim 17, wherein the application is a web application.

30. The system of claim 17, wherein the one or more processors are further configured to receive from the first user an indication of a subset of non-public information to be shared.

* * * * *